(12) United States Patent
Cima et al.

(10) Patent No.: US 10,058,688 B2
(45) Date of Patent: Aug. 28, 2018

(54) MEDICAMENT, METHOD, AND DRUG DELIVERY DEVICE FOR TREATMENT OF OVARIAN CANCER

(71) Applicants: Massachusetts Institute of Technology, Cambridge, MA (US); The General Hospital Corporation, Boston, MA (US)

(72) Inventors: Michael J. Cima, Winchester, MA (US); Hongye Ye, Cambridge, MA (US); Marcela Del Carmen, Boston, MA (US); Michael Birrer, Boston, MA (US)

(73) Assignees: Massachusetts Institute of Technology, Cambridge, MA (US); The General Hospital Corporation, Boston, MA (US)

( * ) Notice: Subject to any disclaimer, the term of this patent is extended or adjusted under 35 U.S.C. 154(b) by 508 days.

(21) Appl. No.: 14/400,216

(22) PCT Filed: May 9, 2013

(86) PCT No.: PCT/US2013/040405
§ 371 (c)(1),
(2) Date: Nov. 10, 2014

(87) PCT Pub. No.: WO2013/170069
PCT Pub. Date: Nov. 14, 2013

(65) Prior Publication Data
US 2015/0080847 A1      Mar. 19, 2015

Related U.S. Application Data

(60) Provisional application No. 61/644,497, filed on May 9, 2012.

(51) Int. Cl.
     *A61M 31/00*      (2006.01)
     *A61K 31/282*      (2006.01)
     *A61M 1/28*      (2006.01)

(52) U.S. Cl.
     CPC ......... *A61M 31/002* (2013.01); *A61K 31/282* (2013.01); *A61M 1/28* (2013.01);
(Continued)

(58) Field of Classification Search
     CPC ........ A61M 31/002; A61M 2210/1017; A61K 9/0092; A61K 9/7007
See application file for complete search history.

(56) References Cited

U.S. PATENT DOCUMENTS 4,795,436 A *    1/1989    Robinson ............. A61K 9/5026
                                                                   424/422
6,350,464 B1 *    2/2002    Dang .................... A61K 9/1647
                                                                   424/426
(Continued)

OTHER PUBLICATIONS

Kumagai S. et al., "Improvement of Intraperitoneal Chemotherapy for Rat Ovarian Cancer Using Cisplatin-Containing Microspheres", Japanese J. of Cancer Research, vol. 87(4):412-17 (1996).
(Continued)

*Primary Examiner* — Aarti B Berdichevsky
(74) *Attorney, Agent, or Firm* — Eversheds Sutherland (US) LLP

(57) ABSTRACT

Drug delivery devices, medicaments, and methods are provided for the intraperitoneal treatment of ovarian cancer. An implantable device for drug delivery includes an elongated, flexible device having a housing defining a reservoir that contains a drug in solid or semi-solid form, and configured to be wholly deployed within the peritoneal cavity of a patient and continuously release a therapeutically effective amount of the drug over a period of at least 24 hours. A medicament includes cisplatin for administration into the
(Continued)

peritoneal cavity of a patient continuously over a treatment period of at least 24 hours. A method of drug delivery includes implanting within the peritoneal cavity of a patient an elongated, flexible device having a reservoir containing a drug, solubilizing the drug at least in part with peritoneal fluid, and releasing an effective amount of the solubilized drug from the reservoir continuously for a period of at least 24 hours.

23 Claims, 11 Drawing Sheets

(52) U.S. Cl.
CPC ..... *A61M 2202/06* (2013.01); *A61M 2205/04* (2013.01); *A61M 2210/1017* (2013.01)

(56) References Cited

U.S. PATENT DOCUMENTS

| | | | |
|---|---|---|---|
| 6,479,067 B1 | 11/2002 | Dang | |
| 6,641,833 B2* | 11/2003 | Dang | A61K 9/1647 424/422 |
| 6,855,331 B2 | 2/2005 | Vook et al. | |
| 8,182,464 B2* | 5/2012 | Lee | A61K 9/0034 424/703 |
| 8,801,694 B2* | 8/2014 | Lee | A61K 9/0034 424/422 |
| 2003/0158598 A1* | 8/2003 | Ashton | A61K 9/0024 623/1.42 |
| 2006/0178655 A1 | 8/2006 | Santini, Jr. et al. | |
| 2007/0197957 A1* | 8/2007 | Hunter | A61L 31/10 604/65 |
| 2007/0202151 A1 | 8/2007 | Lee et al. | |
| 2009/0149833 A1 | 6/2009 | Cima et al. | |
| 2010/0003297 A1 | 1/2010 | Tobias et al. | |
| 2010/0152704 A1* | 6/2010 | Lee | A61K 9/0034 604/517 |
| 2011/0060309 A1 | 3/2011 | Lee et al. | |
| 2011/0202036 A1 | 8/2011 | Boyko et al. | |
| 2014/0350473 A1* | 11/2014 | Lee | A61K 9/0034 604/175 |
| 2016/0374936 A1* | 12/2016 | Martin | A61K 9/0004 604/500 |

OTHER PUBLICATIONS

Rothenberg M., et al., "Combined Intraperitoneal and Intravenous Chemotherapy for Women with Optimally Debulked Ovarian Cancer: Results from an Intergroup Phase II Trial", J. Clinical Oncology, 21(7): 1313-19 (2003).

Terauchi F., et al., "Combination Chemotherapy with Paclitaxel and Intraperitoneal Cisplatin for Ovarian Cancer with Disseminated Lesions in the Peritoneum and the Diaphragm", Int'l J. Clinical Oncology 7(6): 356-60 (2002).

International Search Report and the Written Opinion of the International Searching Authority of PCT/US2013/040405 dated Jul. 18, 2013.

* cited by examiner

MEDICAMENT, METHOD, AND DRUG DELIVERY DEVICE FOR TREATMENT OF OVARIAN CANCER

CROSS-REFERENCE TO RELATED APPLICATIONS

This application claims priority to U.S. Provisional Patent Application No. 61/644,497, filed May 9, 2012, which is incorporated herein by reference.

TECHNICAL FIELD

The present disclosure generally pertains to implantable drug delivery systems and methods. Certain embodiments specifically pertain to systems and methods for local drug delivery and controlled release of drugs in the treatment of ovarian cancer.

BACKGROUND

Ovarian cancer is one of the most common types of cancer, with a prevalence of 13.1 per 100,000 women in the United States and a death rate of 8.8 per 100,000 women. (Horner, et al. (eds.) SEER Cancer Statistics Review (1975-2006)). Ovarian cancer is relatively asymptomatic at its early stages with rare cases of incidental early diagnosis due to other diseases or symptoms. In about three-quarters of all cases of ovarian cancer, the patients present with peritoneal metastasis at the time of diagnosis. (Colombo, et al., *Gynecol. Oncol.* 122, 632-640 (2011)).

The standard primary treatment for advanced ovarian cancer includes cytoreduction surgery where the bulk of the tumor is removed via minimally invasive laparoscopic surgery, followed by intravenous (IV) or intraperitoneal (IP) chemotherapy with a platinum-based agent such as cisplatin.

The IP regimen requires surgeons to implant a catheter connected to a port (such as the BardPort®) during the cytoreduction surgery. Specifically, following the debulking of large visible tumors, two 5 mm incisions are made at the upper right and lower right quadrants of the abdomen. The port is inserted through the incision at the upper right quadrant and sutured subcutaneously. The tip of the catheter is tunneled subcutaneously to the incision in the lower right quadrant of the abdomen where it will enter the peritoneal cavity. Once every three weeks, the patient receives an infusion of 2 liters of cisplatin solution through the port and into the peritoneal cavity.

Although clinical trials have shown that the IP chemotherapy prolongs survival, many patients drop out of treatment due to catheter-related complications. (Armstrong, et al., *N. Engl. J. Med.* 354, 34-43 (2006)). For example, the implantation sites are prone to infection and inflammation over the period of treatment and the long catheter is susceptible to obstruction.

Pharmacokinetic studies have shown that the peak concentration of cisplatin in the peritoneal cavity reaches a level 20 times that in the systemic compartment, and the total area-under-curve concentration of cisplatin is 12 times that of systemic circulation if cisplatin is administered directly into the peritoneal cavity. (Markman, *The Lancet Oncology* 4, 277-283 (2003); Casper, et al., *Cancer Treatment Reports* 67, 235-238 (1983)). The Gynecology Oncology Group has conducted large phase III trials, comparing three different IV cisplatin treatment regimens to IP cisplatin treatment and found the latter to be able to prolong overall survival from 49.7 months in IV treatment to 65.6 months (p=0.03). (Armstrong, et al., *N. Engl. J. Med.* 354, 34-43 (2006)). However, 83% of subjects completed all cycles of IV therapy, but only 42% of subjects completed all cycles of IP therapy. The primary reason for dropping-out of IP treatment is catheter-related complications.

Furthermore, many medical practitioners hesitate to recommend the IP treatment modality due to the lack of familiarity among clinicians with peritoneal administration and catheter-placement techniques. This complex procedure currently can only be performed at premier cancer centers by trained personnel. Accordingly, there is a need for an alternative to IP administration that eliminates catheter-related complications to allow more patients to enjoy the benefits of IP therapy.

Alternative approaches to IP administration have been proposed, such as formulating cisplatin with a polymeric matrix material, for example in particle form, to provide a depot for extended release of the drug. Reported depot approaches involve drug laden polymeric particles that are administered to the desired site and release the drug over a period of time. One disadvantage of polymeric particles is that they require a significant amount of polymeric material in the formulation to reliably control the release of the cytotoxic agent. The mass of polymer significantly exceeds the mass of drug in such formulations. For example, repeated administration could result in the accrual of polymeric materials within the patient and could limit the frequency of administration possible. Another disadvantage of this approach is that the drug administration is essentially irreversible. Thus, if the dosage is administered for the entire therapy, one cannot readily, if at all, remove the drug if the therapy is not tolerated. A third disadvantage of polymeric particle administration is that release from such formulations is strongly affected by the chemistries of the drug and polymeric material. Consequently, the rate of release is limited once the materials are selected, and varying release rates is very complicated. For example, bulk polymers, such as polylactic acid, result in non-zero order releases while a constant, zero-order release rate is often preferred in drug delivery.

Liposomes have also emerged as a popular drug-carrying vehicle in recent years; however, for the same reasons as with the polymer materials, these formulations are not ideal for the treatment of ovarian cancer.

Paclitaxel is another commonly used drug in the current ovarian cancer treatment. It is dosed IV 135 mg/kg post-surgery over 24 hours or IP 60 mg/kg on Day 8. It is a hydrophobic small molecule that has a log P of about 3.5 (DrugBank, DB01229). Several patents disclose incorporating paclitaxel into degradable polymer microparticles for drug release locally. For example, U.S. Pat. No. 6,855,331 to Vook et al. discloses releasing hydrophobic drugs using the polylactic glycolic acid (PLGA) particles. However, the PLGA particles could only sustain a relatively linear release profile up to about Day 11 before a sharp drop in the release rate was observed. Those microparticles could only release for up to 25% of the paclitaxel loaded into the microparticles before the plateau.

In another example, U.S. Pat. No. 6,479,067 to Dang discloses a method of using poly(phosphoester) particles to release paclitaxel and other small molecules such as lidocaine, cisplatin, and doxorubicin. The release of cisplatin from these microparticles, however, is not well controlled, as 45% of the loaded cisplatin was released through Day 1 in one of the in vitro release experiments, and another 30% was released in the subsequent 3 days. In another in vitro release experiment with cisplatin, only 5% of cisplatin was released over 3 days, and almost no cisplatin was released over the rest of the 14 days of in vitro release. The release of paclitaxel was the most consistent among all the drugs mentioned.

The only in vivo efficacy study performed was with OVCAR-3 ovarian tumor cell line which compared microparticles containing palictaxel at a dose of 10 and 40 mg/kg to free paclitaxel of 10 and 40 mg/kg. The results showed that at the 10 mg/kg dose, there is no significant difference between the microparticle formulation and free paclitaxel (70 and 60 days respectively); at 40 mg/kg, the median survival of microparticle formulation is about 110 days, while that of free paclitaxel is about 70 days. This dose is quite high compared with conventional dosing in mice. The standard maximum dose of paclitaxel in the mouse model is 20 mg/kg. (Balthasar, et al., *Cancer Chemother. Pharmacol.* 68, 951-958 (2011)). However, 50 mg/kg has been used to investigate the neurophysiological and neuropathological damage in mice. The dose of 20 mg/kg is, therefore, a better comparison between the efficacy of the microparticles and free paclitaxel.

In another proposed alternative therapy, a group from University of California, San Diego recently developed a type of CD44-targeting hyaluronan-based microparticle that can encapsulate cisplatin. (De Stefano, et al., *Cancer Chemother. Pharmacol.* 68, 107-116 (2011)). CD44 is a surface ligand that is expressed on some types of ovarian cancer cells and hyaluronan is a natural ligand for CD44. However, these particles can only increase cisplatin uptake for CD44-positive ovarian cancer cell lines. Although these particles managed to prolong cisplatin half-life in the peritoneal cavity (when administered IP) to 124 minutes from 18 minutes in IP bolus injection, it still decreased quickly.

Accordingly, a new ovarian cancer treatment regimen that avoids the prolonged use of a catheter, eliminates or minimizes the use depot matrix materials in the drug formulation, is inexpensive, and is simple to administer would be favorable for both clinicians and patients. A significant need therefore exists for new systems and methods for local drug delivery and controlled release of drugs in the treatment of ovarian cancer. Improved systems and methods for continuous or extended intraperitoneal delivery of drug are needed.

SUMMARY

In one aspect, a medicament for use in the treatment of ovarian cancer is provided, including cisplatin for intraperitoneal administration into the peritoneal cavity of a patient continuously over a treatment period of at least 24 hours. In one embodiment, the cisplatin is released continuously from a drug delivery device implanted in the peritoneal cavity of the patient.

In another aspect, a method of intraperitoneal delivery of drug to a patient is provided, including (i) implanting within the peritoneal cavity of a patient an elongated, flexible device which includes a housing defining a reservoir that contains a drug in solid or semi-solid form, (ii) solubilizing the drug at least in part with peritoneal fluid, and (iii) releasing an effective amount of the solubilized drug from the reservoir into the peritoneal cavity continuously for a period of at least 24 hours. In one embodiment, the patient is in need of treatment for ovarian cancer and the drug includes cisplatin or another chemotherapeutic agent.

In yet another aspect, an implantable device for intraperitoneal drug delivery is provided, including an elongated, flexible device which includes a housing defining a reservoir that contains a drug in solid or semi-solid form, wherein the device is configured to be wholly deployed within the peritoneal cavity of a patient and continuously release a therapeutically effective amount of the drug over a period of at least 24 hours.

DETAILED DESCRIPTION

Figure 1A:
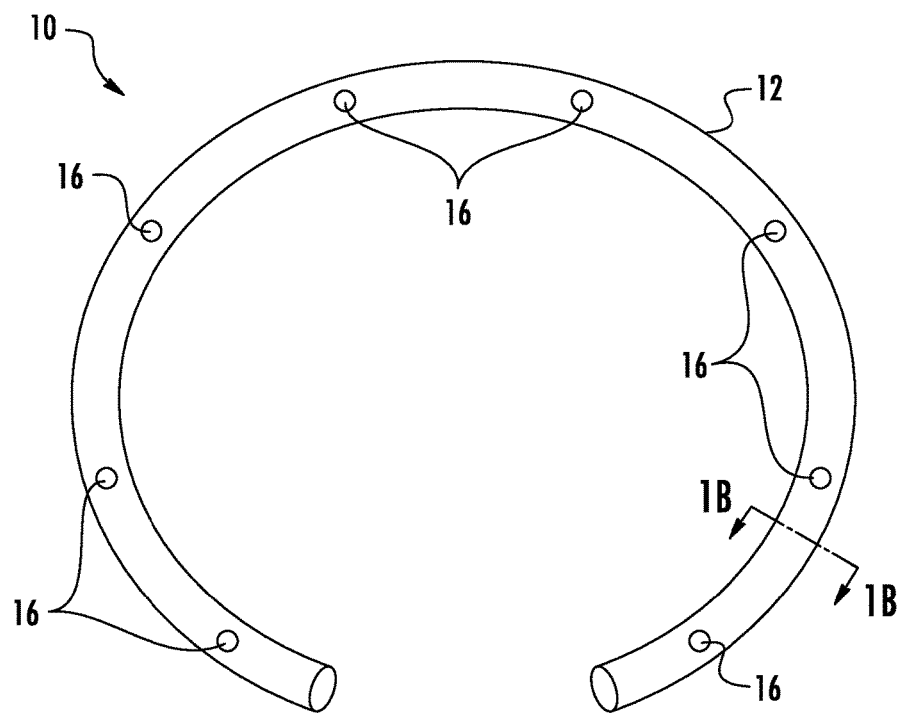
FIG. 1A is a plan view of an implantable drug delivery device in accordance with one embodiment of the present disclosure.

Drug delivery devices, medicaments, and methods are provided to address some or all of the above-described needs. In particular, a reservoir-based drug delivery device that can improve the current treatment regimen for patients with advance-staged ovarian cancer has been developed. These devices and methods advantageously may decrease morbidity due to catheter related complications, reduce systemic drug concentration, and improve patients' well-being during the treatment. The devices and methods have been shown to control tumor growth without causing significant side effects in a mouse model, strongly suggesting its usefulness and benefits, for example, in the treatment of ovarian cancer in human patients.

In certain embodiments, the device is an implantable medical device designed for local, continuous intraperitoneal release of one or more drugs over an extended period. In particular, the devices, medicaments, and methods can be used in intraperitoneal (IP) chemotherapy, such as with a platinum-based drug, such as cisplatin. In particular, the device may be a reservoir-based drug delivery device that can release cisplatin and/or other drugs in a highly reproducible and controlled manner.

Advantageously, the device is implanted once and therefore poses no problem of a "carry over" effect in terms of foreign material between multiple administrations associated with conventional catheter-based IP infusions. In addition, the device advantageously is less dependent on the relative chemistries of the drug and device components, as is the case with conventional formulation-based approaches for extended drug delivery. Moreover, the rate of release can be tuned by varying the architecture of the device, independently of the payload and method of loading.

Advantageously, the reservoir-based device has a high packing ratio for the drug and, therefore, alleviates the problem of having a large volume of fluid infused into the peritoneal cavity. In addition, the chance of an infection or inflammation is minimal because the need for a catheter is eliminated. Lastly, the device can release cisplatin or other drugs at a low and constant rate at the tumor site, thereby greatly reducing the systemic concentration and achieving less drug side effects such as nephrotoxicity.

In certain embodiments, the drug delivery device is designed to be fully deployed in the peritoneal cavity of a patient in need of treatment. For example, the surgeon may leave the device in the peritoneal cavity through the laparoscopic ports during cytoreduction surgery, instead of the tunneling procedure, before closing the wound. Such an approach should eliminate catheter-related complications and improve surgeon acceptance. Removal of the device may be accomplished by minimally invasive surgery using laparoscopy. In other embodiments, the device is constructed of a resorbable material so that no procedure is required to remove the device from the patient after release of the drug.

The Examples described below include preclinical results for local delivery of cisplatin in an animal model of ovarian cancer. Notably, the device described in the study below will release continuously for up to 18 weeks, allowing cisplatin to constantly act on the tumor cells over the entire treatment period. The in vitro release experiment proved that device is able to release linearly and reproducibly, and by engineering the number of release orifices, device dimensions, and/or other features of the device, the drug release rate may be controlled precisely.

I. Implantable Drug Delivery Devices

Certain embodiments of implantable drug delivery devices provided herein generally include a reservoir defined by/within a housing configured for intraperitoneal administration. The housing also may be referred to herein as the "device body" or the "wall." The housing houses (e.g., contains) a drug formulation and then releases the drug from the reservoir following implantation in a patient.

Figure 1B:
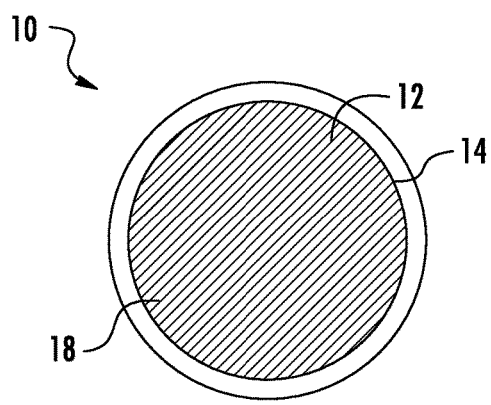
FIG. 1B is a cross-sectional view of the implantable drug delivery device of FIG. 1A, along line B-B.
Figure 2:
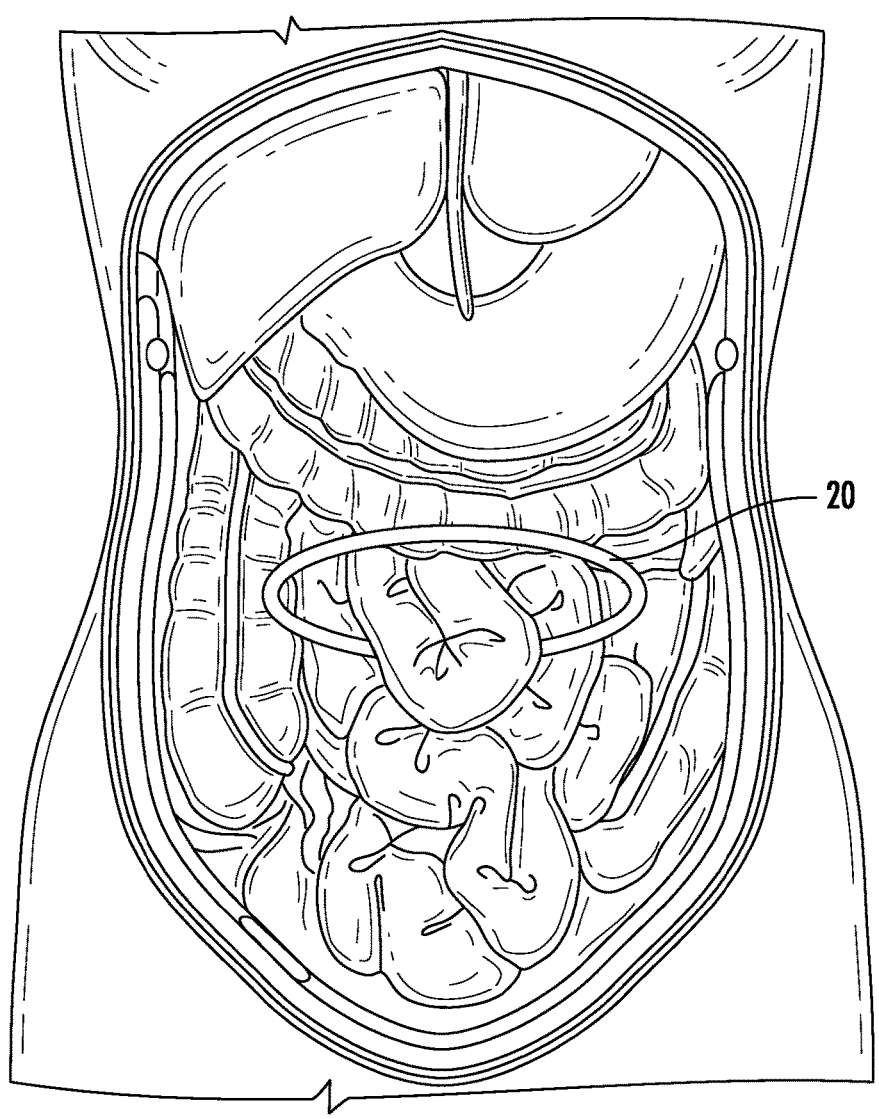
FIG. 2 depicts a drug delivery device implanted in the peritoneal cavity of a human patient in accordance with one embodiment of the present disclosure.

Non-limiting embodiments of the device are shown in FIGS. 1A-B and 2. As shown in FIGS. 1A and B, the housing 12 of the device 10 may be a flexible, annular cylinder, with closed ends, with the reservoir 14 being the defined by the inner surface of the annular cylinder wall. Drug formulation 18 fills the reservoir 14 defined by the inner wall of housing 12. The device may be elongated and flexible. In embodiments, the housing is sized and shaped for implantation wholly within the peritoneal cavity. FIG. 2 depicts the device 20 implanted in the peritoneal cavity of a human patient.

In one embodiment, as shown in FIG. 1A, the device 10 has a tubular-shaped housing 12 with one or more apertures 16 extending through the housing wall in spaced positions along the length of the device 10. In addition, or in an alternative embodiment, one or more orifices may be provided in one or both ends of the housing.

The housing may be formed from material that is elastomeric, which may reduce trauma to surrounding tissues upon implantation. In one embodiment, the housing is sufficiently elastic, even while the reservoir is loaded with drug, to have a curled conformation, which may be elastically straightened during implantation through a laparoscopic port, and elastically return to the original curled conformation following release into the peritoneal cavity. For example, the housing may be formed of silicone.

Release of the drug may be controlled by the housing. For example, drug may be released throughout the entire length of the housing wall or a selected portion thereof. The housing may have one or more holes or apertures to provide a passageway for a physiological fluid in the IP cavity, at the site of deployment of the device in the patient, to flow into the reservoir to solubilize a solid drug formulation disposed therein. In addition or alternatively, the housing wall, or portions thereof may be water permeable or porous to permit the physiological fluid to flow into the reservoir to solubilize the solid drug formulation. The solubilized drug may be released through all or a portion of the housing. For example, the solubilized drug may diffuse through the housing wall itself or through one or more apertures provided in selected areas of the housing wall. Selected areas of the housing wall, e.g., dimpled areas, may be made relatively thinner than other parts of the housing wall to promote diffusion therethrough.

As used herein, the term "solubilized" includes pure solutions as well as suspensions of drug particles dispersed in a liquid carrier. Such suspensions may include microparticulate or nanoparticulate forms of the drug.

The delivery rate of drug from the housing may be affected by the shape, size, number and placement of the apertures. Other factors also may affect the delivery rate, such as the dissolution profile of the drug formulation. In alternative embodiments, release of the drug from the device may involve other mechanisms, such as osmotic pressure or surface erosion. In still other embodiments, the device may operate by a combination of release mechanisms.

The exact configuration and shape of the device may be selected depending upon a variety of factors including the location, route, and method of implantation, the composition and dosage of the drug formulation, the therapeutic application of the device, or a combination thereof. The device may be designed to deliver a therapeutically effective dose of the drug into the peritoneal cavity for local or regional effect.

In certain embodiments, the device is substantially filled with a solid or semi-solid form of the drug. Such configurations may maximize the drug payload on board the device, reducing the size of the device needed to deliver a therapeutically effective dose of the drug over an extended period. For example, the drug formulation desirably is a substantial fraction of the total volume of the entire device at the time of implantation. For example, the drug formulation portion may be more than 50%, more than 70%, more than 90%, e.g., between 75% and 95% inclusive, of the total volume of the drug-loaded device. In certain embodiments, the solid or semi-solid drug formulation includes the drug in an amount of more than 50 percent by volume, more than 75 percent by volume, or more than 90 percent by volume of the reservoir, and one or more excipients in a remaining amount of volume of the reservoir.

The drug delivery device may be sized and shaped for implantation wholly within the peritoneal cavity. The outer surface of the device may be soft and smooth without sharp edges or tips, so as to avoid damaging tissues adjacent to the implanted device. In some embodiments the portion of the device implanted within the peritoneal cavity may have dimensions that do not exceed 3 mm in width or diameter. This generally will facilitate the device being able to pass through an internal bore of a cannula or other laparoscopic access instrument inserted into the peritoneal cavity. In certain embodiments, the device housing has an outer diameter from about 1 mm to about 5 mm. The length of the device can vary, but generally will not be larger than necessary to possess the reservoir volume required to hold the desired drug payload. For example, the device housing may have a length from about 25 mm to about 500 mm, from about 25 mm to about 100 mm, or from about 50 mm to about 100 mm. In embodiments, the desired device dimensions may be calculated from experimental data.

For example, the cisplatin concentration to be maintained in the peritoneal cavity in human patients should be very close to that for mice. The tumors in humans that remain after debulking surgery are less than 1 cm in diameter while the larger tumors growing in the peritoneal cavity of the mice are also about 1 cm in diameter. The volume of peritoneal fluid in human is, however, much larger than that of mice. A simple method of estimating the volume difference is using the body surface area, which is linearly proportional to the volume of blood. The average body surface area of a mouse is 0.0075 $m^2$ while that of a human adult is about 1.85 m, or about 247-times larger. The clearance half-life from the peritoneal cavity in human is about 50 minutes, while that of mouse is about 25 min. Therefore, the targeted release rate to be achieved in human should be approximately 100 times that of in mice. As discussed below, a treatment efficacy study showed that the average cisplatin release rate is 23.6±5.0 μg/day in mice. Accordingly, an approximate human device release rate may be around 2.4 mg/day.

In embodiments, the device is configured to administer cisplatin in vivo at an average rate from about 0.5 mg/day to about 31 mg/day. In a preferred embodiment, the device is configured to administer cisplatin in vivo at an average rate from about 1.5 mg/day to about 3.5 mg/day. For example, the device may be configured to maintain a concentration of the cisplatin in the peritoneal fluid of the patient of at least about 0.5 μg/mL for at least 7 days, while releasing at an average rate of no more than 5 mg/day.

In one embodiment, the device is configured to release the cisplatin in vivo at a rate from about 0.5 mg/hour to about 10 mg/hour. For example, the device may release the cisplatin in vivo at a rate from 0.6 mg/hour to about 2.5 mg/hour.

In one embodiment of a device capable of administering in vivo (e.g., in peritoneal fluid) the therapeutic amounts of cisplatin described above, the device is configured to release cisplatin in vitro at a rate from about 15 mg/day to about 50 mg/day in phosphate buffered saline at 37° C. In other embodiments, the rate may be outside of this range.

The current treatment regimen for cisplatin is 100 mg/$m^2$ per dose, one dose for every 3 weeks, for 6 doses. The total payload for a human device, assuming the same treatment period of 18 weeks, is thus estimated to be 781 mg. In certain embodiments, the device contains from 500 mg to 1000 mg cisplatin. There is most likely also a correlation between the body surface area of the patient and payload of the device. In one case, for example, the device housing may comprise an 8 mm outer diameter, 5 mm inner diameter tube. Therefore, assuming a density of about 1 g/$cm^3$ for the cisplatin powder, and a packing factor of 50%, the device housing would be about 80 mm long. Alternatively, if one wished to deploy and retrieve the device through the lumen of a laparoscope, the outer diameter would likely be smaller. For example, if the housing had an outer diameter of 4 mm and an inner diameter of 2 mm, then the length of the housing would be approximately 497 mm in order to hold the same drug payload. One skilled in the art can readily envision variations of this device design and design criteria with different drugs, housings, animal models, and the like.

In some embodiments, it may be easier to deploy and retrieve two or more such shorter devices. The advantage of such an approach is that no one device may be so long that it is difficult to deploy and retrieve. In addition, proper distribution of drug release within the IP cavity may be best achieved by distributing devices within the cavity. The two or more shorter devices optionally may be tethered together, for example to facilitate retrieval.

In some embodiments, the housing defines multiple reservoirs, which may facilitate releasing two or more separate drug formulations from a single device, releasing drugs at two or more different release rates, releasing drugs at two or more different times following implantation, or combinations thereof. For example, a first dose of the drug may be pre-programmed to release at a first time and a second dose of the drug may be pre-programmed to release at a second, later time. The term "pre-programming" herein generally refers to designing and building the device to provide the selected release functionality.

In certain embodiments, the housing may be made from one material or a combination of materials. The materials desirably are biocompatible and suitable for implantation into a patient. The housing generally is made of a biocompatible polymeric material. In some embodiments, the housing includes a material that is permeable to fluid. The permeable material enables selective intake of fluid into the reservoir to solubilize the drug in the reservoir. Alternatively, one or more apertures in the housing may be configured to enable the selective intake of fluid into the reservoir to solubilize the drug in the reservoir. As used herein, the term "solubilized" includes solutions of drug, fine suspensions of drug, or a combination thereof. Any portion of the housing may be permeable to a solubilizing fluid, such as the container, the end cap, or portions or combinations thereof. In various embodiments, the housing is selectively permeable to water but is substantially impermeable to drug, limiting or preventing the drug from exiting the device through the housing wall. Alternatively, the housing may be substantially water impermeable.

The device housing may be made of biocompatible, non-resorbable materials (such as silicone) or resorbable (e.g., biodegradable) materials (such as poly(glycerol sebacate)). The biodegradable materials have the advantage of requiring only a single surgery of implantation, without the need to retrieve the device after releasing its payload. Poly(glycerol sebacate) (PGS) is also elastomeric. As used herein, the term "resorbable" means that the housing, or a part thereof, degrades in vivo by dissolution, enzymatic hydrolysis, erosion, or a combination thereof. The degradation may occur at a time that does not interfere with the intended kinetics of release of the drug from the housing. For example, substantial resorption of the housing may not occur until after the drug formulation is substantially or completely released. In another embodiment, the housing is resorbable and the release of the drug formulation is controlled at least in part by the degradation characteristics of the resorbable housing.

In embodiments in which the housing is resorbable, the housing may include one or more biodegradable or bioerodible polymers. Examples of suitable resorbable materials include synthetic polymers selected from poly(amides), poly (esters), poly(ester amides), poly(anhydrides), poly(orthoesters), polyphosphazenes, pseudo poly(amino acids), poly(glycerol-sebacate), copolymers thereof, and mixtures thereof. In a preferred embodiment, the resorbable synthetic polymers are selected from poly(lactic acids), poly(glycolic acids), poly(lactic-co-glycolic acids), poly(caprolactones), and mixtures thereof. Other curable bioresorbable elastomers include poly(caprolactone) (PC) derivatives, amino alcohol-based poly(ester amides) (PEA) and poly(octanediol citrate) (POC). In one embodiment, the housing is formed from a combination of a resorbable polyester, such as poly(lactic acid), and a liquid crystalline polymer (LCP).

Alternatively, the housing may be at least partially non-resorbable. Examples of suitable non-resorbable materials include materials such as medical grade silicone, natural latex, PTFE, ePTFE, PLGA, stainless steel, nitinol, elgiloy (non ferro magnetic metal alloy), polypropylene, polyethylene, polycarbonate, polyester, nylon, or combinations thereof. Other examples of suitable non-resorbable materials include synthetic polymers selected from poly(ethers), poly(acrylates), poly(methacrylates), poly(vinyl pyrolidones), poly(vinyl acetates), poly(urethanes), celluloses, cellulose acetates, poly(siloxanes), poly(ethylene), poly(tetrafluoroethylene) and other fluorinated polymers, poly(siloxanes), copolymers thereof, and combinations thereof. Combinations of any of these materials, or these and other materials, may also be employed.

In one embodiment, the material forming the housing may comprise an "antimicrobial" material, such as a polymer material impregnated with silver or another antimicrobial agent known in the art.

In a preferred embodiment, the housing includes at least one radio-opaque portion or structure to facilitate detection or viewing of the device by a medical practitioner, when the device is deployed in vivo and/or as part of the implantation or retrieval procedure. In one embodiment, the housing is constructed of a material that includes a radio-opaque filler material, such as barium sulfate or another radio-opaque material known in the art. Fluoroscopy may be the preferred method of viewing the device during deployment/retrieval of the device, providing accurate real-time imaging of the position and orientation of the device to the practitioner performing the procedure. Other imaging techniques known in the art also may be used.

In one embodiment, the housing further includes at least one suture loop, to aid in securing the implanted device and avoid or minimize device migration. For example, suture loops may be provided at one or both ends of the device.

The housing may include a drug reservoir aperture or valve (e.g., a septum) or other orifice, so that a fluid can be injected into the reservoir. For example, it may be useful to inject a sterile saline into the device immediately prior to implantation of the device to "kick start" the drug dissolution process and reduce the lag time before drug release begins.

The number of apertures and the size of each aperture may be selected to provide a controlled rate of release of the drug. In embodiments in which the device is intended to operate primarily or exclusively via diffusion, the number and size of the apertures may be selected such that the total aperture size is large enough to reduce or avoid the development of osmotic pressure within the reservoir. In embodiments in which the housing is permeable to water, the total aperture size may also be selected to prevent excessive buildup of hydrostatic pressure within the housing, which may increase the volume of fluid in the reservoir causing the housing to swell. For example, an increase in hydrostatic pressure within the reservoir may be prevented by ensuring the size of the aperture is large enough and/or by spacing a number of apertures about the housing as appropriate. Within these constraints on aperture size and number, the size and number of apertures for a given device or reservoir may be varied in order to achieve a selected rate of drug release.

The drug can include essentially any therapeutic, prophylactic, or diagnostic agent that would be useful to deliver locally into the IP space. As used herein, the term "drug" with reference to any specific drug described herein includes its alternative forms, such as salt forms, free acid forms, free base forms, and hydrates. In embodiments, the drug in the drug formulation may be a prodrug. In various embodiments, the drug formulation may be in a solid form, semi-solid form (e.g., an emulsion, a suspension, a gel or a paste), or liquid form.

In certain embodiments, the drug is water soluble. As used herein, the term "water soluble" refers to a drug that is more than sparingly soluble. For example, the water soluble drug may have a solubility equal to or greater than about 10 mg/mL water at 37° C.

In certain embodiments, the drug delivery device is used to treat cancer. In such embodiments, the drug formulation includes a drug that is used to treat cancerous tumors, such as an antiproliferative agent, a cytotoxic agent, a chemotherapeutic agent, or a combination thereof. In one embodiment, the drug may be selected from cisplatin, carboplatin, oxaliplatin, paclitaxel, and combinations thereof. Other platinum-containing anti-cancer drugs, as well as other classes of anti-cancer drugs, may also be used. The drug formulation may also include a biologic, such as a monoclonal antibody, a TNF inhibitor, an anti-leukin, or the like. The drug treatment may be coupled with a conventional radiation or surgical therapy targeted to the cancerous tissue.

In one embodiment, the reservoir-based device works by allowing peritoneal fluid to enter the device, dissolve the solid or semi-solid drug, and release the drug in solution. As described below, it has been found that the stability of cisplatin is surprisingly preserved within the device during in vivo use. Without being bound by a particular theory, it is believed that the stability is superior over solutions of cisplatin because the drug is in the solid form within the device. This allows for maximum drug efficacy upon release, even months after implantation.

In another embodiment, the drug delivery device may be used to treat infections or for other purposes, such as to manage pain.

In certain embodiments, the drug formulation includes a reduced quantity of excipients, substantially no excipients, or no excipients. In various embodiments, the drug formulation may include at least one excipient, preferably in a minor amount.

Pharmaceutically acceptable excipients are known in the art and may include lubricants, viscosity modifiers, surface active agents, osmotic agents, diluents, and other non-active ingredients of the formulation intended to facilitate handling, stability, dispersibility, wettability, and/or release kinetics of the drug. The excipient generally is not of a type or amount that would be characterized as a matrix material.

In various embodiments, the drug formulation is in a substantially solid form, such as in the form of a drug rod, a drug tablet, a drug pellet, a number of rods, tablets, or pellets, a compact powder (for example in a disk shape) or a combination thereof, although other configurations are possible. In a certain embodiments, the drug formulation is in a solid form in order to reduce the overall volume of the drug formulation and thereby reduce the size of the device.

II. Applications and Use

Medicaments for the IP treatment of ovarian cancer are also provided. In certain embodiments, a medicament includes cisplatin for use in the treatment of ovarian cancer by intraperitoneal administration into the peritoneal cavity of a patient continuously over a treatment period of at least 24 hours. For example, the cisplatin may be released continuously from a drug delivery device implanted in the peritoneal cavity of the patient. The drug delivery device may be a device as described above or other drug delivery devices known in the art.

Methods of treating a patient with a drug delivery device are also provided. As used herein, the term "patient" generally refers to a human patient, but may include other mammals, such as in medical research, veterinary or livestock applications. The drug delivery device may be implanted in the patient to release drug locally to essentially any implantation site in the patient and may be particularly useful for delivering drugs that cause undesirable side effects or result in insufficient bioavailability when delivered systemically. In a preferred embodiment, the implantation site is the peritoneal cavity of a human patient in need of treatment for cancer.

In certain embodiments, the method includes implanting a drug delivery device within a peritoneal cavity of a patient and thereafter releasing the drug from the drug delivery device into the peritoneal cavity. In some embodiments, the method is implemented for treatment of a patient having ovarian cancer. The step of implantation of the drug delivery device may include a minimally invasive procedure or an open surgical procedure. The implantation may be guided using imaging and positioning techniques and navigation systems known in the art.

In one embodiment in which the drug delivery device is preloaded with drug and preassembled, the implantation may include loading the drug delivery device into a delivery instrument and thereafter deploying the drug delivery device from the delivery instrument into an implantation site within the peritoneal cavity. The delivery instrument may include a large bore needle, a cannula, or a catheter, having suitably sized internal bore. For example, the device may be inserted through a working channel of a laparoscopic instrument inserted into the peritoneal cavity. In one embodiment, a sterilized kit is provided that includes the drug delivery device and one or more delivery instruments.

The drug delivery device may be implanted in association with various other medical or surgical procedures. For example, the drug delivery device may be implanted as part of cytoreduction surgery, such as through a laparoscopic port.

Once the device is implanted, the drug formulation is released from the drug delivery device into the peritoneal cavity. In certain embodiments, the drug is released for an extended treatment period, such as for at least 24 hours. For example, the drug may be released over a period of about one day to about six months, for example from 5 to 60 days, or from 10 days to 30 days. In embodiments, the drug is released at a relatively continuous rate over all or at least a majority of the treatment period.

In embodiments in which the drug delivery device houses a drug in solid or semi-solid form, releasing the drug further includes solubilizing the drug. For example, the drug may be solubilized with a physiological fluid passing into the housing from the implantation environment, such a peritoneal fluid. The physiological fluid may pass through an aperture in the drug delivery device. The fluid may also pass through the housing of the drug delivery device, which may be permeable to fluid. Alternatively, an aqueous fluid may be injected into the reservoir to solubilize the drug. In other embodiments, the drug is stored in the device in semi-solid, gel, slurry, or liquid form, in which case the drug may or may not need to be solubilized prior to release.

Release of the drug may be driven at least in part by diffusion. In some embodiments, the release may be driven primarily or exclusively by diffusion. In other embodiments, the release may be driven by diffusion in combination with another release mechanism, in whole or in part. For example, in certain embodiments the release rate may be determined at least in part based on the size of one or more apertures. In some cases, the release rate may be determined primarily or exclusively by the size of the aperture or apertures. In still other cases, the release rate may be further influenced by the location of the aperture, the shape of the apertures, other characteristics of the aperture or device in general, or combinations thereof. In other embodiments, the release of the drug may be driven by the permeability of the device housing wall.

The device may provide extended, continuous, intermittent, or periodic release of a selected quantity of a drug over a period that is therapeutically desirable. In one embodiment, the device can deliver the desired dose of drug over an extended period, such as 5 days, 7 days, 10 days, 14 days, or 20, 25, 30, 45, or 60 days, or more. The rate of delivery and dosage of the drug can be selected depending upon the drug being delivered and the disease or condition being treated. The release kinetics of the device can be tailored by varying the number and size of apertures in the device, varying the composition of the drug formulation therein, among other device and drug parameters.

In some embodiments, the drug delivery device is resorbable. In particular, the housing may be resorbable material, such as a resorbable polyester and a liquid crystalline polymer. In such embodiments, the device may degrade by surface erosion into biocompatible monomers. The device may begin degrading upon implantation and may degrade while the drug is released. After the drug is released, the device may continue degrading to the point of loss of mechanical integrity. For example, the device may degrade over a suitable period. Thus, the method may further include permitting any remaining portions of the device, such as the housing, to degrade in vivo, which may avoid the need for removing or retrieving the device after the drug has been released.

In other embodiments, the drug delivery device is non-resorbable. In such embodiments, the device may be removed following implantation. In one such a case, the method further includes removing the drug delivery device following release of the drug. In still other embodiments, the device may not be removed even though the device is not resorbable.

III. Methods of Manufacture/Assembly

Methods of making an implantable drug delivery device are also provided. In certain embodiments, the method includes forming a drug formulation, forming a housing, and loading the drug formulation into a reservoir in the housing through an opening (such as one at the end of the housing), and then closing off the opening.

In certain embodiments, forming a drug formulation entails forming a drug formulation that includes one or more active pharmaceutical ingredients (APIs), and optionally, one or more excipients. The API may include a chemotherapeutic agent, for example, a platinum-containing chemotherapeutic, such as cisplatin. In some embodiments, the drug formulation includes a limited amount of excipient or is substantially free of excipient, so that a relatively higher percentage of the volume of the drug formulation is API, permitting the delivery of a relatively larger amount of the API with a relatively smaller volume of drug formulation.

In embodiments, forming the drug formulation may include forming a solid or semi-solid drug formulation. This is particularly desirable because a solid or semi-solid drug formulation may require relatively less space in the housing, permitting the delivery of a relatively larger amount of drug formulation from a reservoir of a given size. Methods of forming solid or semi-solid drug formulations generally are known in the art, and include granulating the drug formulation to produce a high concentration drug formulation with specific physicochemical properties (e.g., solubility, dissolution rate). Optionally thereafter, the granulated or powdered drug formulation may be compacted, for example by using a tablet press. Desirably, the compacted solid drug formulation has dimensions and a shape that are substantially similar to that of the reservoir so that it may be easily inserted into and contained in the reservoir.

The reservoir housing may be formed using a variety of methods, such as injection molding, compression molding, extrusion molding, transfer molding, insert molding, thermoforming, casting, or a combination thereof. In one embodiment, the housing is formed using precision injection molding. The housing is formed with a hollow interior, defining a reservoir for holding the drug formulation.

Forming the device housing also may include forming one or more apertures through the housing. In particular embodiments, the aperture is formed through the housing and/or through a wall of the tissue interfacing member, such as by mechanically punching, mechanical drilling, or laser drilling one or more holes, or such as by injection molding, forming, or casting the housing or tubular body with a hole formed therein. Forming an aperture generally includes sizing and positioning the aperture to achieve a selected release rate for the drug formulation once the device is implanted. In certain embodiments, the step of forming the housing may also include forming multiple different drug reservoirs in a single housing, such as by forming one or more partitioning structures in the housing or by inserting one or more partition structures into the housing once formed.

In one embodiment, loading the housing with the drug formulation includes placing the drug formulation in the reservoir in the housing and sealing the housing to contain the drug formulation therein. In embodiments in which the drug formulation is a solid drug formulation, loading the housing may include placing one or more drug rods, pellets, or tablets in the housing. Alternatively, the drug formulation may be in a fluidized form (e.g., melted, in solution with a solvent liquid, or in suspension with a non-solvent liquid) for reservoir loading and then subsequently solidified (e.g., by cooling or volatilization of the liquid). Loading the housing may include filling the reservoir with the drug formulation, maximizing the amount of drug that can be delivered from a device of a given size. Sealing the housing may include plugging the opening (used for loading-in the drug formulation) with a medical-grade adhesive, a solid plug, or combination thereof.

Device assembly may also include associating one or more release controlling structures with the housing, such as a sheath or coating placed over at least a portion of the housing to modulate the passage of water into the housing, or a degradable membrane positioned over or in one or more of the apertures to control the initial time of release of the drug therethrough.

In certain embodiments, the device is assembled using sterile techniques, for example, assembly in a clean room environment and sterilization using ethylene oxide gas, irradiation, or high intensity pulsed light. The sterilization technique will depend upon the sensitivity of the components used, such as the tendency for polymers and drugs to degrade after exposure to radiation. The device then may be vacuum-sealed in a polymeric package prior to distribution to reduce the amount of moisture or air that could potentially cause any one of the components to become contaminated or prematurely decompose during its shelf life.

The present disclosure may be further understood with reference to the following non-limiting examples.

IV. Examples

Materials for in vitro release were obtained from VWR International (USA). Cisplatin, A2780 cell line, nickel(II) chloride, sodium hydroxide, sodium diethyldithiocarbamate trihydrate (DDTC), dimethyl sulfoxide and HPLC-grade methanol were obtained from Sigma-Aldrich (St. Louis, Mo., USA). The HPLC column (ODS Hypersil, 250×4.6 mm, 5 µm) was purchased from Thermo-Scientific (USA). SKOV3-Luc (luciferase-positive) cell line and luciferin were obtained from Caliper LifeSciences (Hopkinton, Mass., USA). Isofluorane was purchased from McKesson (San Francisco, Calif., USA). Cell growth media, MTT assay, fetal bovine serum (FBS) were purchased from Invitrogen (NY, USA). BALB/c and nu/nu mice were purchased from Charles River (MA, USA).

HPLC Sample Preparation

Working solutions of nickel (II) chloride in PBS and DDTC in 0.1M sodium hydroxide were prepared at 0.1 mg/mL and 0.1 g/mL respectively. Nickel chloride was used as an internal standard while DDTC was used to conjugate cisplatin for UV detection on the HPLC machine. The samples were diluted in PBS to a final volume of 500 µL, before adding 50 µL of each of nickel chloride and DDTC stock solutions. The sample was then incubated at 37° C. for 30 minutes before running on HPLC.

HPLC Method

The HPLC method was a modification of the published method by V. Augey, et al. (*J. Pharma. and Biomed. Anal.* 13, 1173-78). An Agilent 1200 LC system was used for cisplatin quantification. The column was heated to 30° C. and the sample holder was cooled to 4° C. prior to the run. A mobile phase of 75% methanol in water was used, with a flow rate of 1.4 mL/min. The cisplatin peak appeared at 5.1 minutes and the internal standard peak at 6.0 minutes. A calibration curve was obtained for a concentration range of 0.1 to 5 µg/mL and was highly linear (r=0.999).

Cisplatin Assay Calibration

Stock cisplatin solution of 1 mg/mL was prepared in saline solution. The stock solution was then serially diluted to 0.1 µg/mL from 5 µg/mL. 50 µL each of the working solutions of DDTC and internal standard was added to 500 µL of the various concentrations of cisplatin. The calibration samples were incubated for 30 min at 37° C. and ran on HPLC with the above-mentioned parameters. A calibration was run on each day that the samples were run to ensure accuracy.

Example 1

Fabrication and Assembly of Proof-of-Concept Reservoir Device

Figure 3:
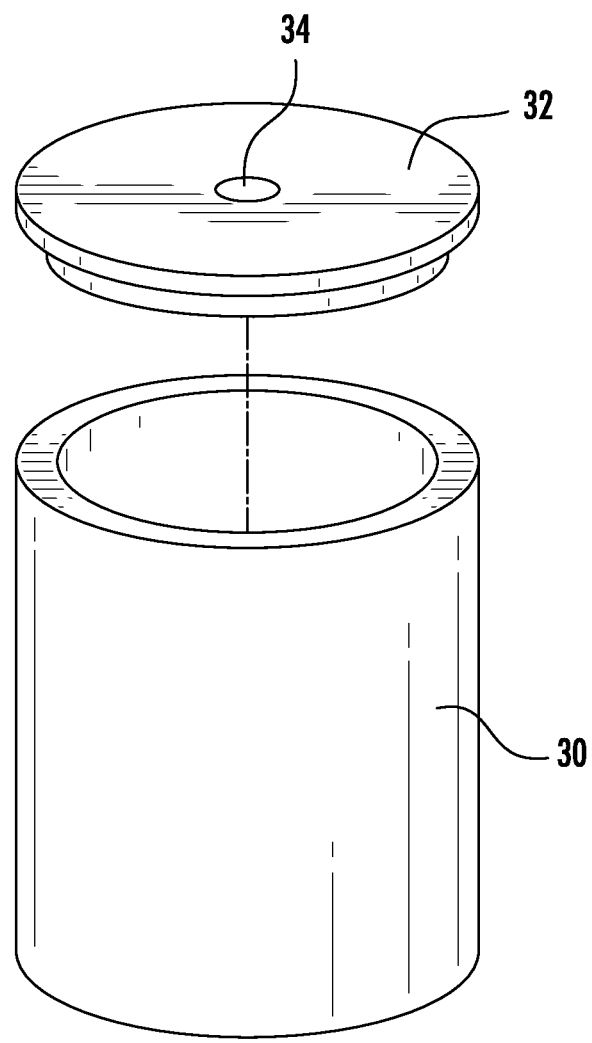
FIG. 3 is an exploded view of a reservoir-based drug delivery device in accordance with another embodiment of the present disclosure.

Reservoir-based drug delivery devices were injection molded from poly-L-lactic acid (PPLA). The cylindrical devices were substantially shaped as shown in FIG. 3 with an outer diameter of about 3 mm, an inner diameter of about 2.5 mm, and a height of about 3.5 mm. Each device housing 30 was loaded with 10 mg of cisplatin powder. Then, the housing was sealed by attaching a cap 32, or lid, over the opening of the housing 32. The lid 32 had a 180 μm orifice 34 drilled through it. The housing components were fabricated by injection molding by Matrix Incorporated (East Providence, R.I., USA). In some devices, additional holes were drilled (on the cylindrical surface of the device housing) with Cameron CNC Micro Machining Center (Sonora, Calif., USA) to create devices having various numbers of apertures, for example one device had 6 total orifices and one device had 11 total orifices.

Example 2

In Vitro Release of Cisplatin from Reservoir Device

Drug release was accomplished by diffusion through the micromachined orifice(s) in the device made in Example 1. Fick's First Law of Diffusion (Equation 1) was used to estimate the rate of drug release from the device.

$$\dot{m} = A + D\frac{C_s}{\Delta x}$$ (Equation 1)

In Equation 1, $\dot{m}$ is the mass diffusion rate (mass per unit time), A is the area of the release orifice (or orifices), D is the diffusion coefficient, $C_s$ is the solubility of the drug and $\Delta x$ is the diffusion distance (assumed to be the depth of the orifice). These reservoir-based devices allow for simple control of the release rate by engineering the size and/or number of orifices.

Figure 4:
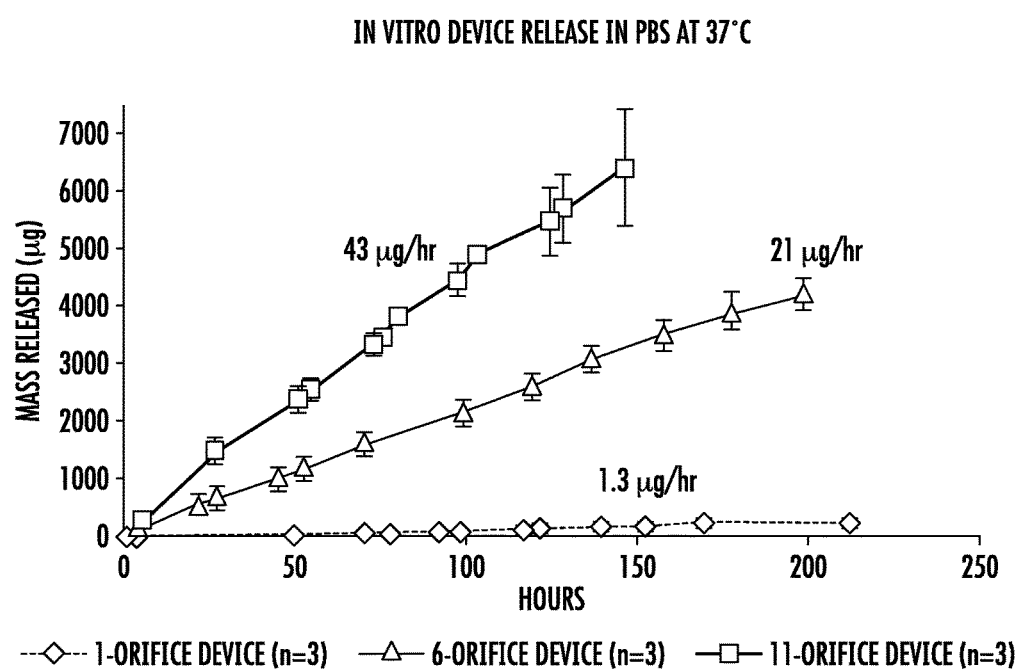
FIG. 4 is a graph showing the in vitro release profile for various reservoir-based drug delivery devices.

The device was first vacuumed in phosphate-buffered saline (PBS) to replace air in the device with PBS. This process "activates" the device by forming a saturated solution inside the device for release. The device was then released in PBS at 37° C. The release solution was changed to a fresh PBS solution at various time points to maintain a constant sink condition around the device. The release solution at each time point was then assayed with HPLC to measure the amount of drug that was released. This was then plotted with time to obtain the in vitro release profile for the device, as shown in FIG. 4. The results showed that the devices release vary linearly and reproducibly. The 6-orifice device released cisplatin at a rate of 21 μg/hour in vitro and the 11-hole device released at 43 μg/hour.

Example 3

In Vitro Cytotoxicity Study

The in vitro cytotoxicity study involved bathing the SKOV3 cells in various concentrations of cisplatin over various periods of time in order to estimate the minimum concentration of cisplatin that the device needs to maintain in the peritoneal cavity to kill tumor cells. The cisplatin-susceptible cell line A2780 and cisplatin-resistant cell lines SKOV3 and OVCAR3 were used. RPMI 1640 with 20% fetal bovine serum (FBS) was used for culturing A2780 and OVCAR3, and McCoy's 5a cell growth media with 10% FBS was used for SKOV3 propagation. The cells were seeded in 96-well plates at $10^4$ cells/well. The cells were then incubated in cell culture media containing cisplatin concentrations of 0.1 to 10 μg/mL over different durations ranging from 2 hours to 7 days. The cisplatin-containing cell media were refreshed daily to prevent degradation of the drug over time. The control wells contained cells that were subjected to cell culture media without cisplatin. The percentage cell viability was calculated as a percentage of the untreated group at each time point.

Figure 5:
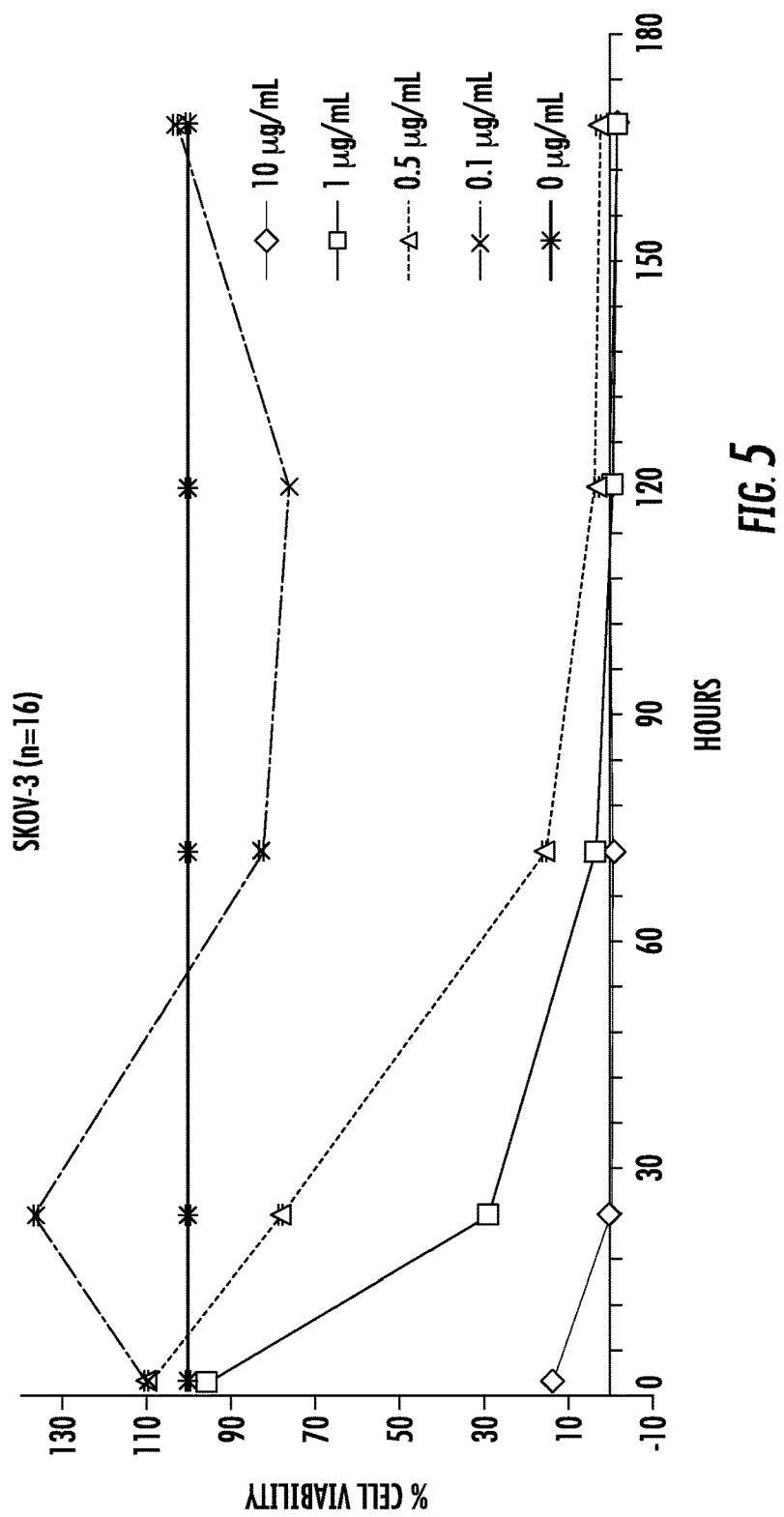
FIG. 5 is a graph showing the cell viability of ovarian cancer cells over time when exposed to various concentrations of cisplatin.

The results are shown in FIG. 5. 10 μg/mL is used as a positive control because it was shown that 10 μg/mL for 2 hours is the critical condition to kill ovarian tumor cells. (Royer, et al., *Anti-Cancer Drugs* 16, 1009-16 (2005)). The results show that 0.1 μg/mL is too low to kill tumor cells over a period of 7 days. A minimum concentration of about 0.5 μg/mL over 7 days should to be maintained to achieve significant tumor cytotoxicity.

Example 4

Pharmacokinetic Study

BALB/c mice were divided into 2 groups: device implantation and IP bolus injection administration. Five 1-orifice devices were implanted for this study. The animals were sacrificed at various time points in groups of 3 after either device implantation or IP bolus injection, to harvest their peritoneal lavage and blood. Peritoneal lavage was obtained by injecting 1 mL of sterile saline into the peritoneum and immediately withdrawing the solution out. The blood sample was allowed to clot for 30 minutes before centrifuging to separate serum from the blood. The lavage and serum samples were assayed for cisplatin concentration and plotted with the time of treatment. All animal protocols had been approved by the Division of Comparative Medicine at MIT.

Figure 6A:
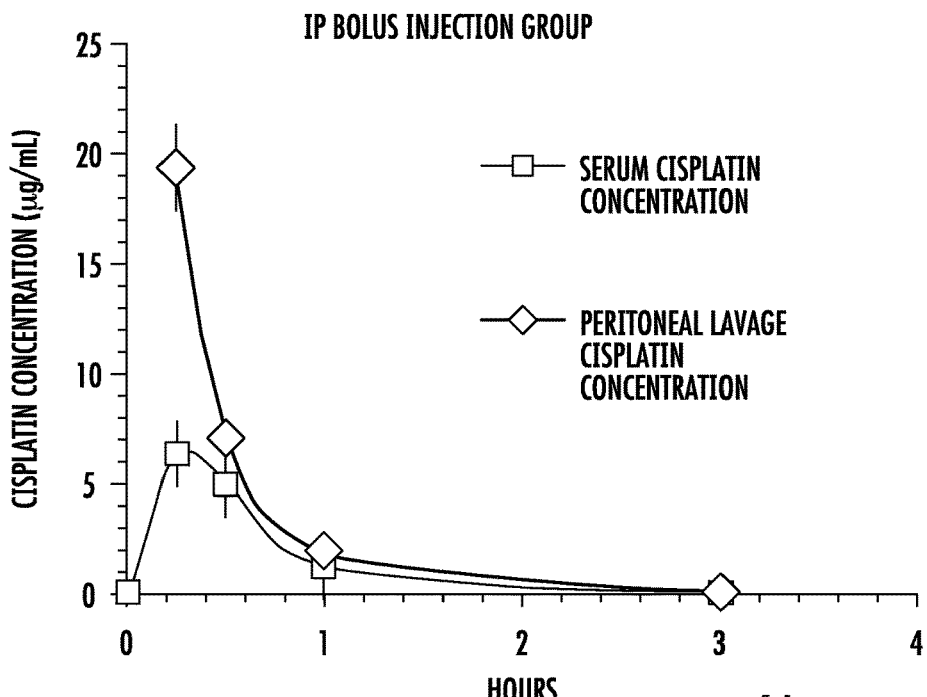
FIG. 6A is a graph showing in vivo cisplatin concentration over time after IP bolus injection.
Figure 6B:
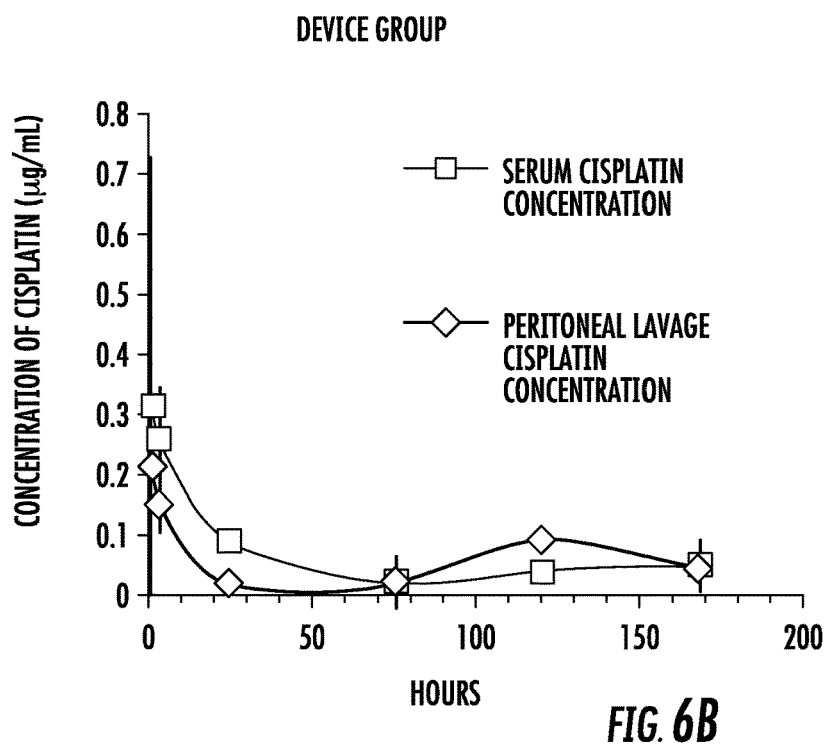
FIG. 6B is a graph showing in vivo cisplatin concentration over time with release from an implanted reservoir-based drug delivery device.

The results of the pharmacokinetics study are shown in FIGS. 6A and B. The results revealed that for IP bolus injection, the serum cisplatin concentration spiked at about 7 μg/mL and quickly decreased to below detection level in about 3 hours. The device group, however, was able to constantly maintain a very low serum concentration of about 0.1 μg/mL. The device group was also able to maintain a concentration of 0.1 μg/mL in the peritoneal cavity over 7 days while the IP bolus injection group quickly dropped to zero in about three hours. The concentration of peritoneal cisplatin concentration that the single-orifice reservoir-based device maintained is below the minimum cisplatin concentration for killing cancer cells. A 6-orifice device (21 μg/hour release rate) was, therefore, used for the subsequent experiments.

Example 5

Tumor Induction Study

The tumor induction study was performed in nu/nu mice to validate the animal model and to elucidate the tumor growth profile. This study established the protocol for the subsequent drug treatment study. $5\times10^5$, $10^6$, $5\times10^6$, $10^7$ SKOV3 luciferase-positive cells suspended in their cell culture media were inoculated in each nu/nu or SCID BEIGE mouse at Day 0. The tumors were allowed to grow for up to 35 days and the luminescence intensity was measured twice a week. 10 μg/g of luciferin stock solution (15 mg/mL in sterile DPBS) was injected, and then after 10 minutes, the tumors were imaged.

Figure 7:
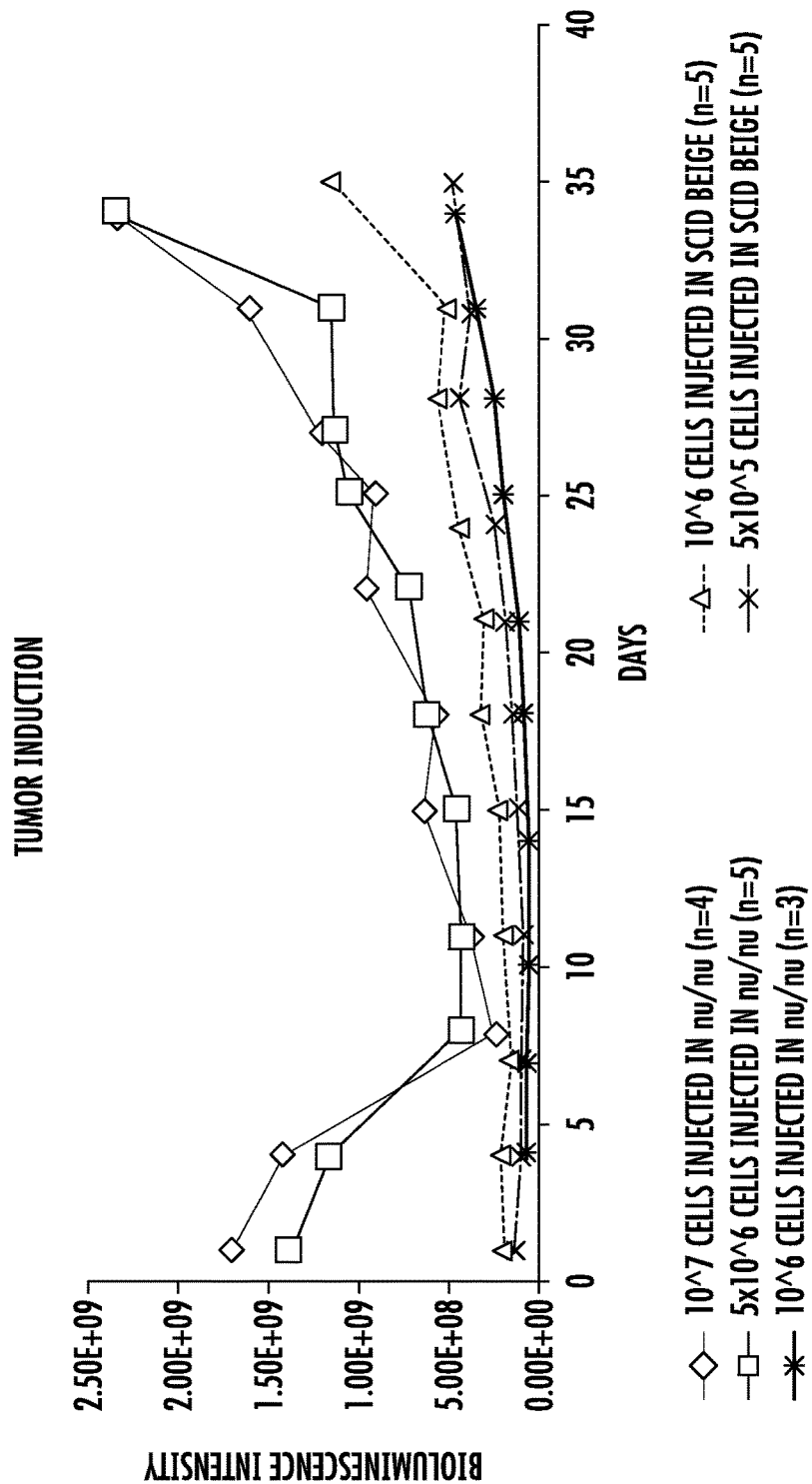
FIG. 7 is a graph showing in vivo tumor growth over time in mice injected with various concentrations of SKOV3 luciferase-positive cells.

The results are shown in FIG. 7, which shows an initial drop in the bioluminescence value of $5\times10^6$ and $10^7$ cells/animal. Presumably this is the result of only some of the cells remaining viable over time or these cells being attacked by the mouse's immune system. The tumor cells that survived seeded at various locations in the peritoneal cavity and stabilized by about 7 days. This initial drop in bioluminescence intensity is not observed for the lower cell number injections, indicating that $5\times10^6$ and $10^7$ cells/animal is likely to be excessive. The tumors began to grow exponentially from about Day 21 onwards.

Patients who receive chemotherapeutic treatment in the clinic are treated after tumor-debulking surgery where the only tumors remaining are small and diffuse. Treatment in this animal model is therefore started before the exponential tumor growth, on Day 14, in order to mimic the clinical situation. The animals that were injected with $5\times10^6$ and $10^7$ cells/animal developed tumors which grew rapidly and formed one or two tumors larger than 1 cm in diameter in about 50 days. This disease presentation did not mimic the clinical scenario. The tumors that remain after surgical tumor resection in patients are distributed throughout the peritoneal cavity, ideally each with a diameter of less than 1 cm.

At Day 14, the tumors for the $10^7$ and $10^6$ cells/mouse were visually compared. A reduction of tumor size was observed and the tumors were better dispersed in the peritoneal cavity at $10^6$ cells/mouse. A later experiment involving treatment of these SCID BEIGE mice revealed that due to their severely defective immune system, the mice were significantly less tolerant to cisplatin treatment and the study had to be terminated prematurely. Subsequent experiments proceeded with $10^6$ cells/mouse inoculation in nu/nu mice.

Example 6

Treatment Efficacy

The nu/nu mice were inoculated with tumor cells on Day 0 and treatment was started on Day 14. $10^6$ SKOV3 cells were inoculated into the mice on Day 0 and treatment (either IP bolus injection at 5 mg/kg or intraperitoneal device implantation) was administered on Day 14. The animals were divided into three groups: device group, IP bolus injection at once per week (1x/wk) and untreated control. The devices were sterilized with ethylene oxide prior to implantation. All animal care guidelines as listed in the animal protocol were followed. The animals were imaged 2 times a week, similar to the tumor induction study. The animals in the toxicity study were sacrificed on day 56 and their organs (kidney, liver, spleen, intestines and bone) were removed immediately upon euthanasia to be fixed in 10% formalin overnight. The devices from the animals with a device implanted were also retrieved during necropsy. The amount of drug remaining inside the device was measured with HPLC to determine the quantity of drug that has been released.

Figure 8:
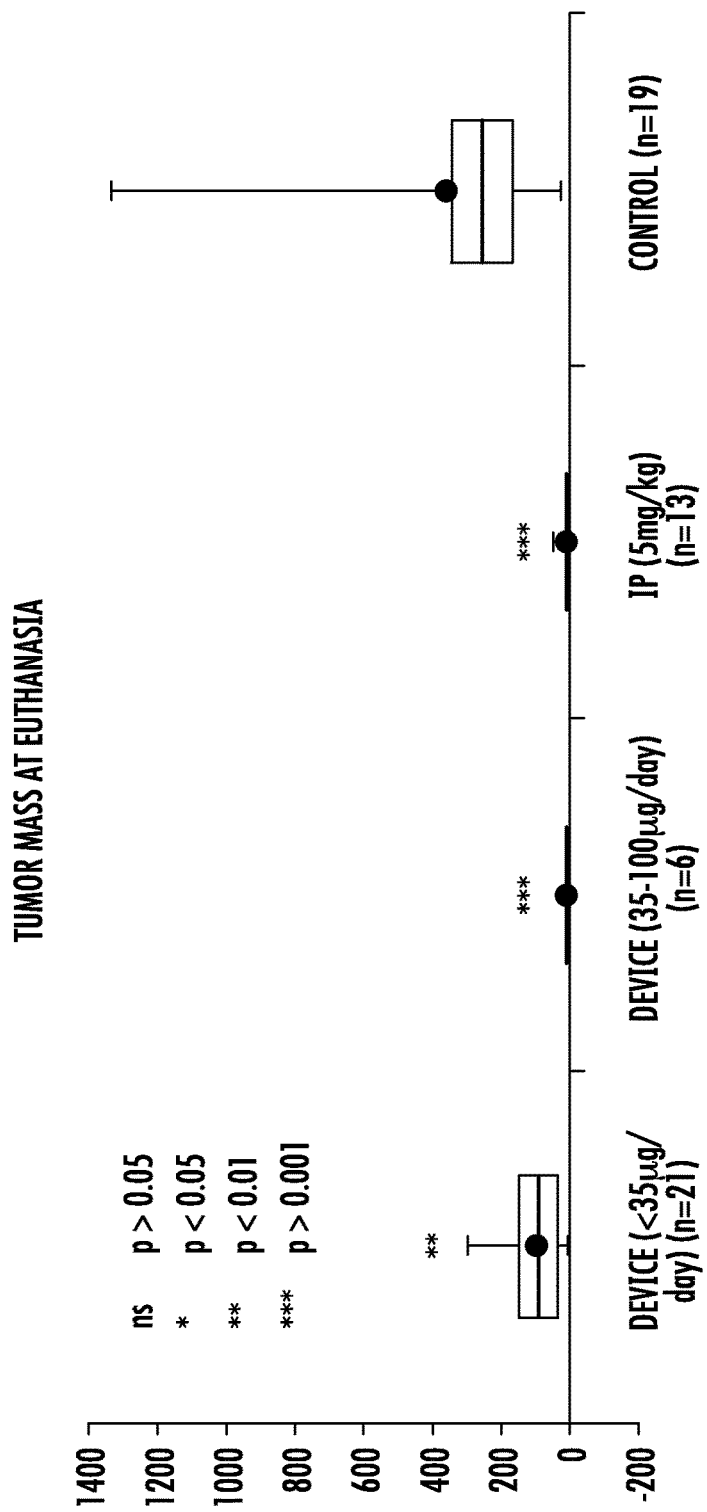
FIG. 8 is a graph showing the comparative tumor mass of mice having received various IP cancer treatments.
Figure 9:
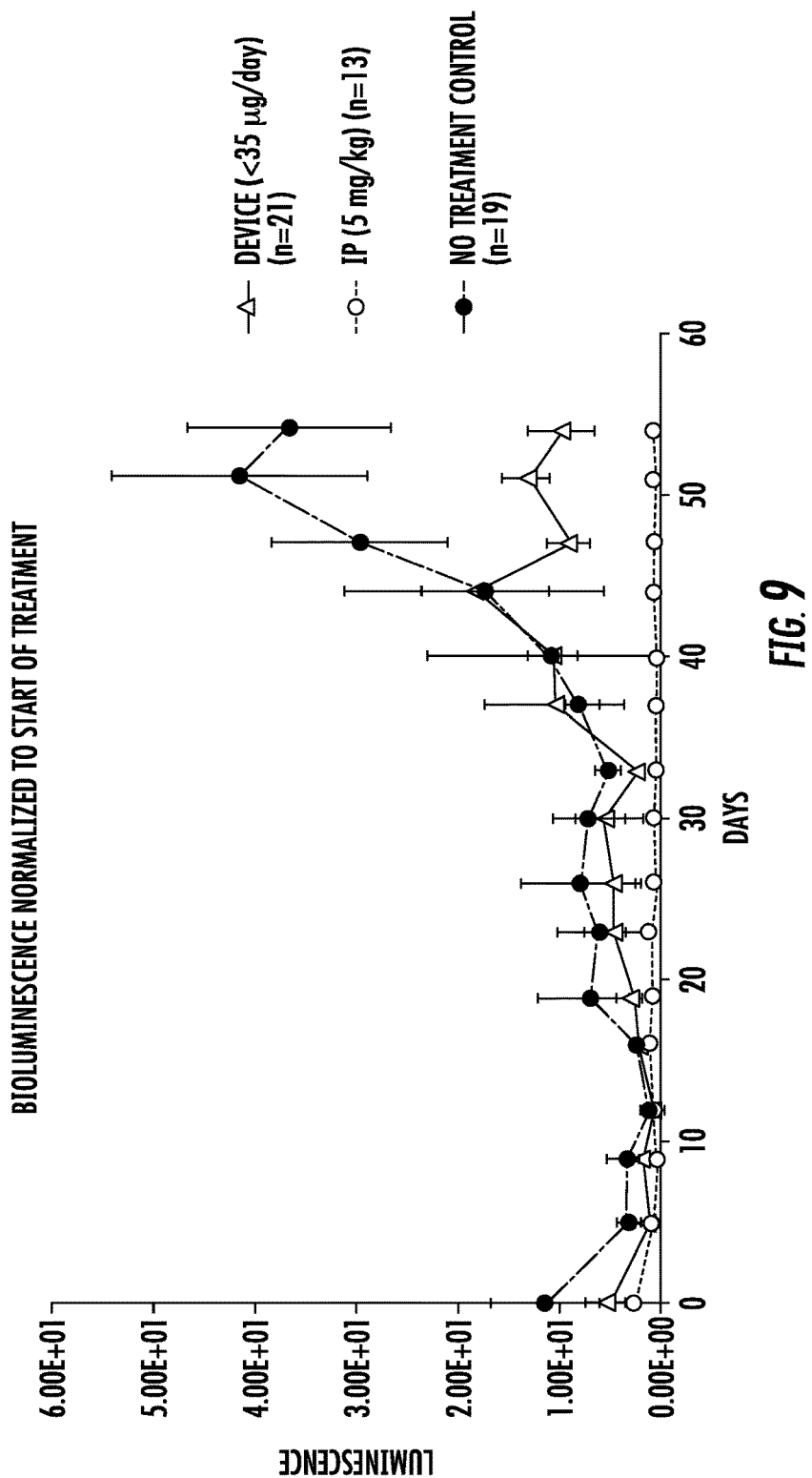
FIG. 9 is a graph showing in vivo tumor growth over time in mice having received various IP cancer treatments.

Devices with different release rates were tested in the animals. It was shown the study that the devices that released less than 35 µg/day (a range of 13-32 µg/day) allowed the animals to survive until the end of the study. This preliminary data offers significant insight into the physiologically relevant dose required for tumor burden reduction without systemic toxicity. FIG. 8 illustrates the significant tumor mass reduction observed in the device and IP treatment groups. The normalized luminescence in FIG. 9 reflects the relative tumor burden measured in the device treatment (for release rates <35 ug/day), IP bolus treatment (weekly 5 mg/kg), and no treatment control groups.

Example 7

Toxicity Study

Figure 10:
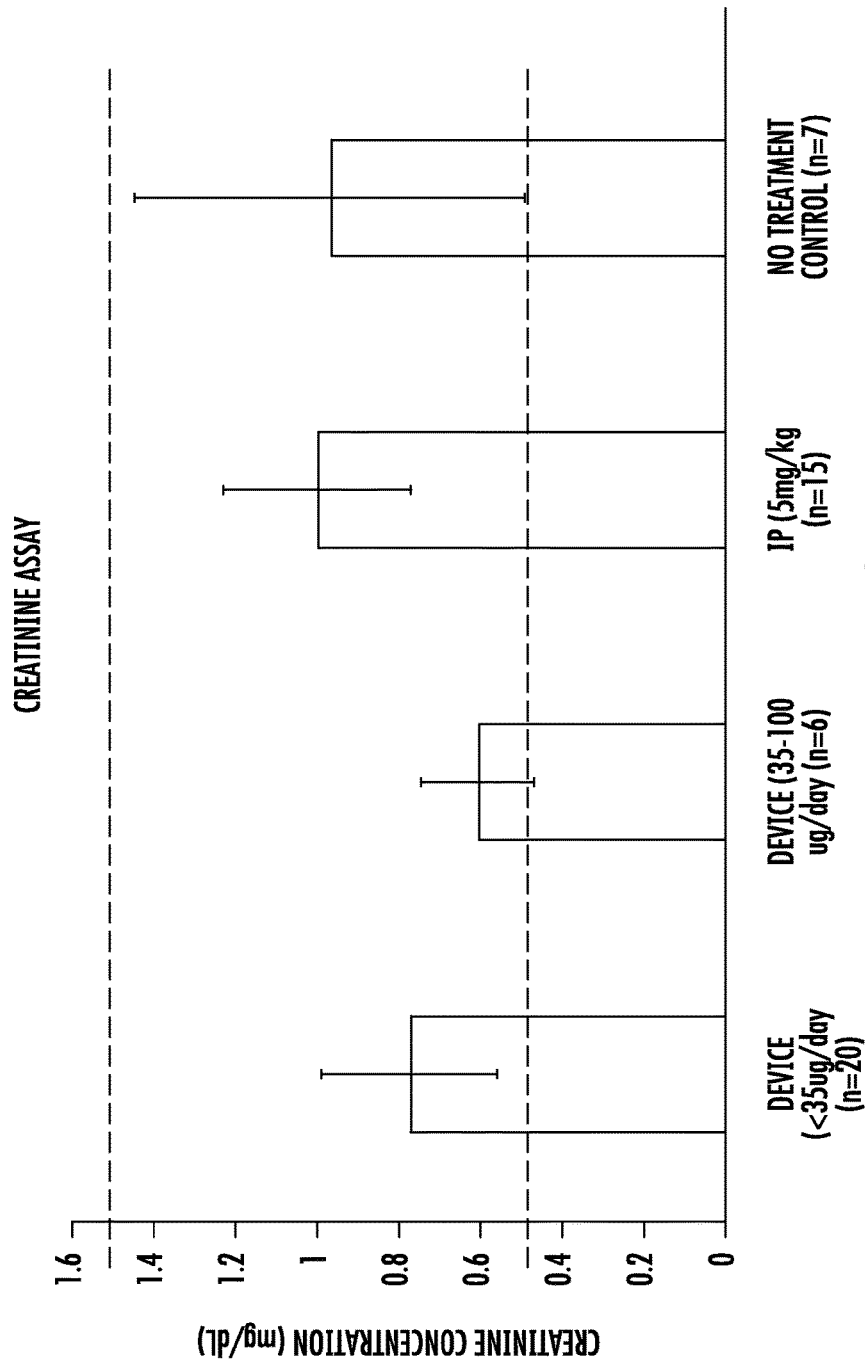
FIG. 10 is a graph showing the relative creatinine concentrations in mice having received various IP cancer treatments.

The animals from the treatment efficacy study above were euthanized at the end of the experiment and their organs were harvested for histological analysis. Serum samples were also harvested for the analysis of creatinine levels in the various groups. H&E stain showed that there was no significant kidney damage in any group of animals. FIG. 10 also shows that there was no significant increase in serum creatinine levels, indicating no nephrotoxicity in any of the groups. Normal creatinine levels are shown in red.

Figure 11:
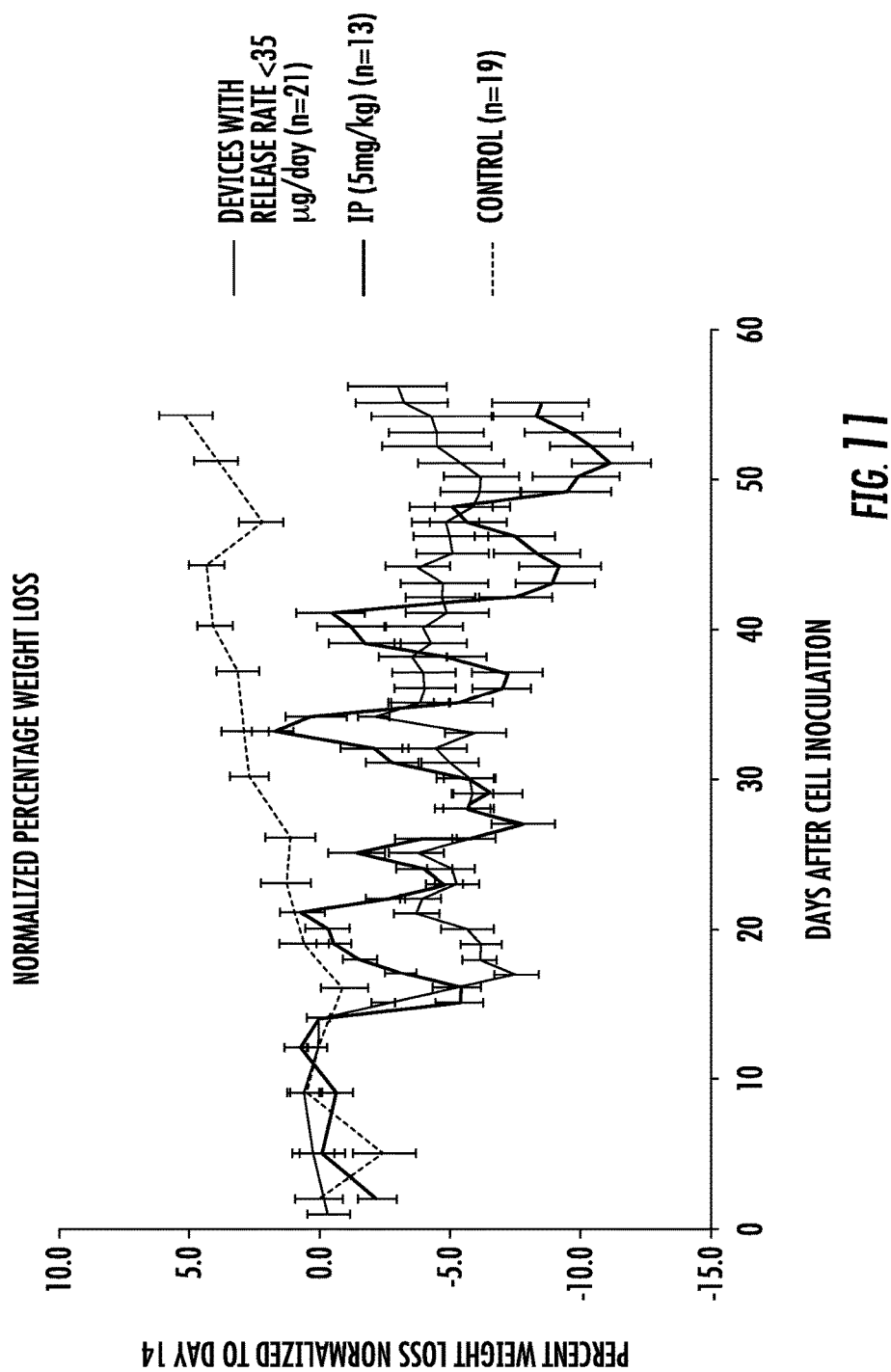
FIG. 11 is a graph showing the relative weight loss over time of mice having received various IP cancer treatments.

Bone marrow depletion was the main toxicity observed. Bone marrow depletion was observed in mice that received more than 35 µg/day from the devices and in the IP bolus group, as compared to the controls. The toxicity was significantly more pronounced in the IP group with major loss of myeloid and erythroid cells in the bone marrow. There was no significant bone marrow depletion from devices with a dose of less than 35 µg/day. The weight loss throughout the duration of the study illustrated in FIG. 11 also reflects the relative degree of systemic toxicity observed in the three groups. The weekly IP bolus injection is clearly toxic with an observed drop in body weight with every dose. The body weight recovers by about 7 days post-dose, however, with repeated dose, significant systemic toxicity is observed.

The SKOV3 tumor resistance cell line was chosen as the animal model. This cell line was obtained from the ascites fluid of a human epithelial ovarian cancer patient, and therefore is a good representation of metastatic tumors of the ovaries in the peritoneum. The North American Firefly Luciferase gene was a stable transfection from a CMV promoter and had been shown to express the luciferase gene over 13 generations. Only cells of less than 10 generations were used for all the animals so that the luminescence intensity would be representative of the actual tumor burden. While bioluminescence is not a precise measurement of the tumor load in the animals, it was not feasible to sacrifice a significant number of animals at every time point to track tumor growth. Moreover, even if the tumor masses were measured at each time point, the small tumors embedded in the mesenteric fats could be easily missed out, resulting in inaccuracies. Therefore, bioluminescence tracking is a reasonable method to follow tumor growth in this study.

The treatment efficacy study included a group of animals which were treated with IP bolus injection (10 mg/kg) at a frequency of 1 dose per week. Tumors in this group remained relatively small. Nephrotoxicity differences between the 11-orifice device group and the IP bolus injection 1 dose per week group show that there is significant tubular damage in the latter. The pharmacokinetics study suggested that the lower serum cisplatin concentration is most likely the reason for this toxicity difference. Thus, the 11-orifice device was able to bring about maximum treatment efficacy with minimum renal damage and was proven to be an ideal treatment modality through both preliminary in vitro and in vivo studies. Accordingly, the medicaments, devices, and methods described herein may decrease morbidity due to catheter related complications, reduce systemic drug concentration, and improve patients' well-being during the treatment.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. A method of intraperitoneal delivery of drug to a patient comprising:
    implanting within a peritoneal cavity of the patient an elongated, flexible device which comprises a housing defining a reservoir that contains a drug in solid or semi-solid form, wherein the drug comprises cisplatin;
    solubilizing the drug at least in part with peritoneal fluid; and
    releasing an effective amount of the solubilized drug from the reservoir into the peritoneal cavity continuously for a period of at least 24 hours.

2. The method of claim 1, wherein the housing comprises a first end, a second end, and an annular wall defined between the first and second ends, wherein the reservoir is defined by an inner surface of the annular wall.

3. The method of claim 2, wherein the annular wall comprises one or more apertures extending therethrough, the one or more apertures providing areas of egress of solubilized drug from the device.

4. The method of claim 1, wherein the solid or semi-solid form comprises:
    the drug in an amount of more than 50 percent by volume of the reservoir; and
    one or more excipients in a remaining amount of volume of the reservoir.

5. The method of claim 1, wherein the solid or semi-solid form comprises:
    the drug in an amount of more than 75 percent by volume of the reservoir; and
    one or more excipients in a remaining amount of volume of the reservoir.

6. The method of claim 1, wherein the solid or semi-solid form comprises:
    the drug in an amount of more than 90 percent by volume of the reservoir; and
    one or more excipients in a remaining amount of volume of the reservoir.

7. The method of claim 1, wherein the implanting comprises inserting the device through a working channel of a laparoscopic instrument inserted into the peritoneal cavity.

8. The method of claim 1, wherein the device is implanted in the peritoneal cavity during cytoreduction surgery.

9. The method of claim 1, wherein the patient is in need of treatment for ovarian cancer.

10. The method of claim 1, wherein the patient is human.

11. The method of claim 10, wherein the device is configured to release the cisplatin in vitro at a rate from about 15 mg/day to about 50 mg/day in phosphate buffered saline at 37 ° C.

12. The method of claim 10, wherein the device is configured to release cisplatin in vivo at a rate from about 0.5 mg/day to about 30 mg/day.

13. The method of claim 10, wherein the average rate of release of cisplatin is from about 1.5 mg/day to about 3.5 mg/day.

14. A method of intraperitoneal delivery of cisplatin to a human patient in need of treatment for ovarian cancer, the method comprising:
    implanting within the patient's peritoneal cavity at least one elongated, flexible device which comprises a housing defining a reservoir that contains cisplatin; and
    releasing the cisplatin from the at least one device into the peritoneal cavity continuously in an amount effective to maintain a concentration of the cisplatin in the peritoneal fluid of the patient of at least about 0.5 µg/mL for at least 7 days.

15. The method of claim 14, wherein the average rate of release of the cisplatin is no more than 5 mg/day.

16. The method of claim 14, wherein the average rate of release of the cisplatin is from 1.5 mg/day to 3.5 mg/day.

17. The method of claim 14, wherein the device is configured to release the cisplatin in vitro at a rate from about 15 mg/day to about 50 mg/day in phosphate buffered saline at 37 ° C.

18. The method of claim 14, wherein the cisplatin in the reservoir during the implanting is in a solid or semi-solid form, and where the method further comprises solubilizing the cisplatin at least in part with peritoneal fluid to effect the release of the cisplatin from the device.

19. The method of claim 18, wherein the housing comprises a first end, a second end, and an annular wall defined between the first and second ends, the reservoir being bounded by an inner surface of the annular wall, wherein the annular wall comprises one or more apertures extending therethrough, the one or more apertures providing egress of the solubilized cisplatin from the device.

20. A method of intraperitoneal delivery of cisplatin to a human patient in need of treatment of ovarian cancer, the method comprising:
    implanting within the patient's peritoneal cavity an elongated, flexible device which comprises a housing defining a reservoir that contains cisplatin in solid or semi-solid form;
    solubilizing the cisplatin within the reservoir at least in part with peritoneal fluid; and
    releasing the solubilized cisplatin from the reservoir into the peritoneal cavity continuously in an amount effective to maintain a therapeutic concentration of the cisplatin in the peritoneal fluid of the patient, wherein the average rate of release of the cisplatin is from 1.5 mg/day to 3.5 mg/day.

21. The method of claim 20, wherein the cisplatin is released over a period from 5 to 60 days.

22. The method of claim 20, wherein the cisplatin is released over a period from 10 to 30 days.

23. The method of claim 20, wherein the housing comprises a first end, a second end, and an annular wall defined between the first and second ends, the reservoir being bounded by an inner surface of the annular wall, wherein the annular wall comprises one or more apertures extending therethrough, the one or more apertures providing egress of the solubilized cisplatin from the device.

* * * * *